United States Patent [19]

Hirose et al.

[11] Patent Number: 5,010,174

[45] Date of Patent: Apr. 23, 1991

[54] NOVEL CALCITONIN DERIVATIVE AND SALT THEREOF

[75] Inventors: Sachio Hirose, Tokyo; Motomu Hane; Masanobu Inagawa, both of Ibaraki, all of Japan

[73] Assignee: Mitsubishi Petrochemical Co., Ltd., Tokyo, Japan

[21] Appl. No.: 353,336

[22] Filed: May 17, 1989

Related U.S. Application Data

[63] Continuation-in-part of Ser. No. 215,280, Jul. 5, 1988, abandoned.

[30] Foreign Application Priority Data

Jul. 8, 1987 [JP] Japan .................................. 62-168583
Feb. 17, 1988 [JP] Japan .................................. 63-32888
Nov. 24, 1988 [JP] Japan .................................. 63-294761

[51] Int. Cl.$^5$ ................................................ C07K 7/36
[52] U.S. Cl. ..................................... 530/307; 530/324
[58] Field of Search ................................ 530/307, 324

[56] References Cited

U.S. PATENT DOCUMENTS 4,212,795  7/1980  Hughes et al. ...................... 530/307
4,622,386 11/1986  Orlowski et al. ................... 530/307
4,820,804  4/1989  Orlowski et al. ................... 530/307
4,845,080  7/1989  Fisher et al. ....................... 530/307

Primary Examiner—Lester L. Lee
Attorney, Agent, or Firm—Oblon, Spivak, McClelland, Maier & Neustadt

[57] ABSTRACT

There is disclosed a calcitonin derivative and its salt, comprising an amino acid residue at the 1-position of calcitonin which is a cyclic amino acid residue represented by the formula:

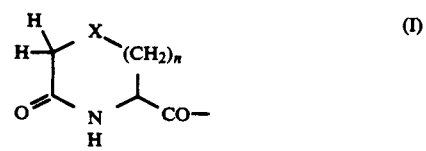

wherein X represents a sulfur atom or a methylene group; and n represents an integer of 0 or 1. and an amino acid residue at the 7-position which is a cysteine residue which may be substituted with an appropriate protective group.

5 Claims, No Drawings

NOVEL CALCITONIN DERIVATIVE AND SALT THEREOF

This application is a continuation-in-part application of our U.S. Ser. No. 215,280 filed on July 5, 1988 now abandoned.

BACKGROUND OF THE INVENTION

This invention relates to a novel calcitonin derivative and a salt thereof having the action of lowering the serum $Ca^{2+}$ level and useful as the therapeutic for osteoporosis, bone Paget's disease, digestive hypercalcemia, etc.

Calcitonin (hereinafter called "CT") is a peptide hormone occuring in thyroid glands of various mammals such as human being, or ultrabranchial glands of fish, cyclostomi and birds. The hormone exhibits an action antagonistic to parathyroid hormone, and has been known to act on bone and lower the $Ca^{2+}$ level in blood. Up to date, CT has been extracted and purified from human being, bovine, porcine, sheep, rat, chicken, salmon, eel, and its amino acid primary sequence has been clarified. These animal-derived CT are all polypeptides comprising 32 amino acids, and are common in that the cysteine residues at the 1- and 7-positions form a disulfide bond, and the carboxy group terminal end (hereinafter called the "C-terminal") is prolineamide.

These CT are expected to be therapeutics for osteroporosis, bone Paget's disease or digestive hypercalcemia.

However, the disulfide bond possessed by CT is estimated to be very unstable in a solution to bring about probably lowering in physiological activity, and therefore, utilization as a pharmaceutical has been very limited. As a means for solving this problem, a derivative having α-amino-suberinic acid residue

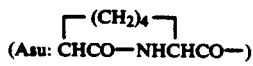
(Asu: CHCO—NHCHCO—)

(hereinafter called 1,7
"Asu—CT")

in place of cystine residue

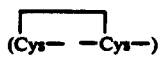

was synthesized. This derivative had high CT activity and yet exhibits high stability in a solution, and was therefore useful as a pharmaceutical.

However, since 1,7
Asu —CT contains Asu, it involves the problem that its synthesis is complicated, namely can be synthesized only by the liquid phase method in peptide chemistry, and the solid phase method which is the simple and rapid synthetic method is not applicable. Accordingly, in order to obtain a derivative having high activity and high stability, which can be synthesized by the solid phase method, and consequently found that the above object can be accomplished by converting the amino acid residue at the 1-position of calcitonin to a specific cyclic amino acid residue, to accomplish the present invention.

The abbreviated names, the abbreviated symbols to be used in the present specification have the following meanings.

1. About Amino Acids

Ala: alanine, Arg: arginine, Asn: asparagine, Asp: aspartic acid, Cys: cysteine, Gln: glutamine, Glu: glutamic acid, Gly: glycine, His: histidine, Ile: isoleucine, Leu: leucine, Lys: lysine, Met: metionine, Phe: phenylalanine, pro: proline, Ser: serine, Thr: threonine, Trp: tryptophan, Tyr: tyrosine, Val: valine,

cystine, Oct: 3-oxo-5-carboxyperhydro-1,4-thiazine, Kpc: 2-keto-piperidine -6-carboxylic acid, pGlu: pyroglutamic acid.

In some cases, the respective symbols may show the corresponding amino acid residues.

2. About Protective Groups

Boc: t-butyloxycarbonyl, Fmoc: 9-fluorenylmethyloxycarbonyl, $Bu^t$: t-butyl, Bzl: benzyl, $Cl_2.Bzl$: 2,6-dichlorobenzyl, Z: benzyloxycarbonyl, Cl.Z: 2-chlorobenzyloxycarbonyl, Npys: 3-nitropyridinesulphenyl, OBzl: benzyl ester, $OBu^t$: t-butyl ester, OcHex: cyclohexyl ester, Tos: tosyl, Br.Z: 2-bromobenzyloxycarbonyl, Mtr: 4-methoxy-2,3,6-trimethylbenzenesulfonyl, For: formyl, Acm: acetamidomethyl, M.Bzl: 4-methoxybenzyl, $4CH_3.Bzl$: 4-methylbenzyl, Trt: trityl, $SBu^t$: t-butylmercapto, CA: carbamoylmethyl, CM: carboxymethyl, AE: aminoethyl.

3. About Reagents

DCC: dicyclohexylcarbodiimide, HOBt: 1-hydroxybenzotriazole, DTT: dithiothreitol, DCM: dichloromethane, DMF: dimethylformamide, DMSO: dimethyl sulfoxide, MeOH: methanol, TEA: triethylamine, TFA: trifluoroacetic acid, HF: hydrofluoric acid, HCl: hydrogen chloride or hydrochloric acid, $CH_3CN$: acetonitrile, Tris.HCl: tris(hydroxymethyl)aminomethane hydrochloride.

SUMMARY OF THE INVENTION

The present invention concerns a calcitonin derivative and its salt, comprising an amino acid residue at the 1-position of calcitonin which is a cyclic amino acid residue represented by the formula:

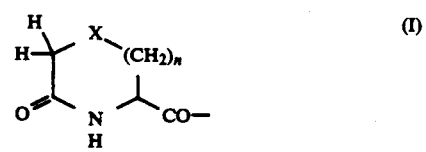

wherein X represents a sulfur atom or a methylene group; and n represents an integer of 0 or 1. and an amino acid residue at the 7-position which is a cysteine residue which may be substituted with an appropriate protective group.

DESCRIPTION OF THE PREFERRED EMBODIMENTS

Calcitonin refers to a natural type calcitonin, comprising 32 amino acid residues extructed from human being, bovine, procine, sheep, rat, chicken, salmon, eel, etc. and purified, a synthetic calcitonin (e.g., calcitonin as disclosed in Japanese provisional Patent Publications No. 47498/-1986 and No. 233699/1986, U.S. Pat. Nos. 4,616,012, U.S. Pat. No. 4,497,732, U.S. Pat. No. 4,604,238, U.S. Pat. No. 4,605,515, U.S. Pat. No. 4,605,514, U.S. Pat. No. 4,604,237 and U.S. Pat. No. 4,604,236) and a calcitonin derivative.

As the amino acid residue at the 1-position, particularly Oct, Kpc and pGlu are preferred, and pGlu is the most preferred.

The cysteine residue which is the amino acid residue at the 7-position may be protected with an appropriate protective group.

The protective group for such cysteine residue may be a protective group for mercapto group conventionally used in peptide chemistry, including $4CH_3.Bzl$ group, Acm group and Trt group used as the protective group during synthesis of peptide, or CA group, CM group, AE group, etc. which is introduced by the reaction of mercapto group with a modifying agent. Particularly, Acm group and CA group are preferred.

The amino acid residues at other positions than the 1- and 7-positions are not particularly limited, provided that they can constitute calcitonin, and examples may include those as set forth below:

2-position: Ala, Ser or Gly
3-position: Ser, Asn, Thr or Ala
4-position: Leu
5-position: Ser
6-position: Thr
8-position: Val or Met
9-position: Leu
10-position: Gly or Ser
11position: Lys, Thr or Ala
12-position: Leu or Tyr
13-position: Ser, Thr or Trp
14-position: Gln, Lys or Arg
15-position: Glu, Asp or Asn
16-position: Leu or Phe
17-position: His or Asn
18-position: Lys or Asn
19-position: Leu, Phe or Tyr
20-position: Gln or His
21-position: Thr or Arg
22-position: Tyr or Phe
23-position: Pro or Ser
24-position: Arg, Gln or Gly
25-position: Thr or Met
26-position: Asp, Asn, Ser, Gly or Ala
27-position: Val, Thr, Ile or Phe
28-position: Gly
29-position: Ala, Ser, Val or Pro
30-position: Gly or Glu
31-position: Thr Val or Ala Of these amino acid residues, particularly the combination of the amino acid residues constituting chicken calcitonin, eel calcitonin and salmon calcitonin as well as the combination of the amino acid residue at the 3-position is Thr or Ala are preferred.

Further, in the present invention, it is preferred that in addition to the 1-position of the calcitonin being a specific cyclic amino acid residue, the 3-position is Thr or Ala, particularly Thr, and the cystein residue at the 7-position is that protected by an acetamidomethyl (Acm) group, since such a calcitonin is excellent in activity and stability as well as extremely easy in synthesis.

Specific examples of the calcitonin derivatives of the present invention are as shown below.

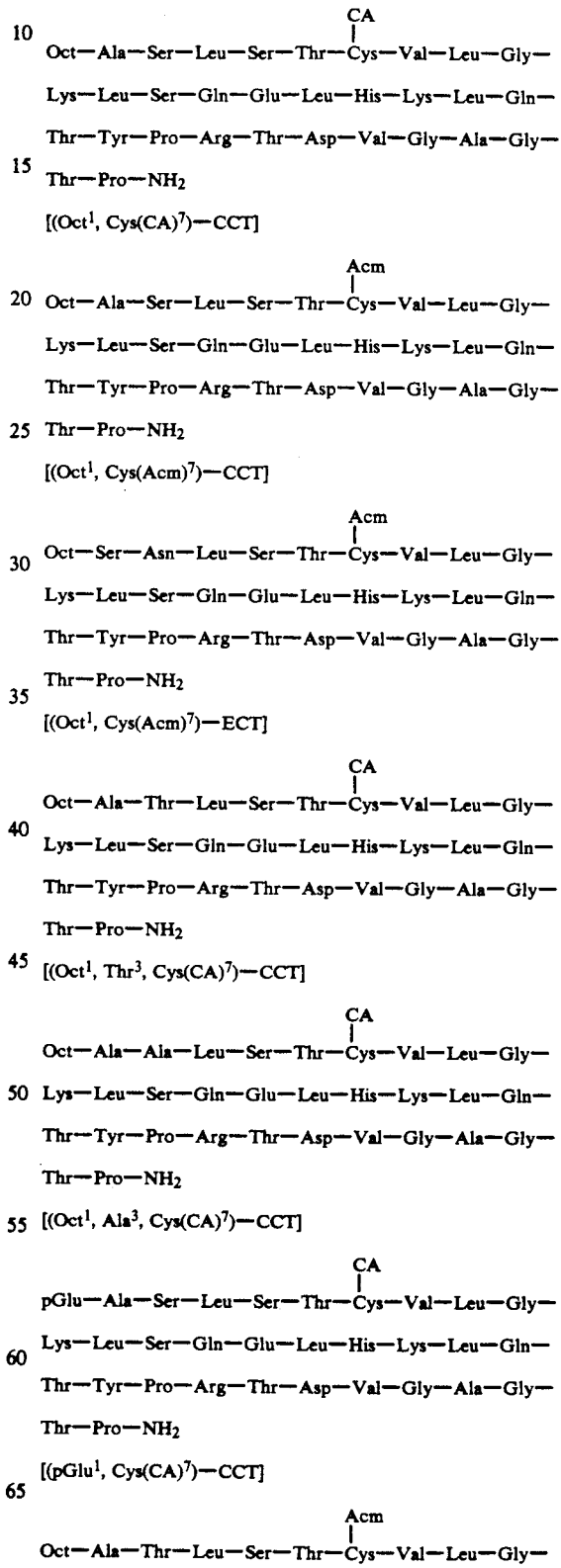

-continued

Lys—Leu—Ser—Gln—Glu—Leu—His—Lys—Leu—Gln—

Thr—Tyr—Pro—Arg—Thr—Asp—Val—Gly—Ala—Gly—

Thr—Pro—NH$_2$

[(Oct$^1$, Thr$^3$, Cys(Acm)$^7$)—CCT]

```
                    Acm
                     |
pGlu—Ala—Thr—Leu—Ser—Thr—Cys—Val—Leu—Gly—
```

Lys—Leu—Ser—Gln—Glu—Leu—His—Lys—Leu—Gln—

Thr—Tyr—Pro—Arg—Thr—Asp—Val—Gly—Ala—Gly—

Thr—Pro—NH$_2$

[(pGlu$^1$, Thr$^3$, Cys(Acm)$^7$)CCT]

wherein CCT represents chicken calcitonin and ECT represents eel calcitonin, hereinafter the same.

The calcitonin derivative of the present invention may be in the form of a salt with a mineral acid such as hydrochloric acid, sulfuric acid, phosphoric acid, etc. or an organic acid such as acetic acid, citric acid, etc., or it may be also in the form of a metal salt such as of sodium, potassium, calcium, etc., or a salt with ammonia or an organic base such as dicyclohexylamine, pyridine, etc.

The calcitonin derivative of the present invention can be synthesized according to the solid phase method or the liquid phase method conventionally used for synthesis of peptides. This synthesis can be performed according to the methods as described in Hand book of Biochemical Experiments, Vol. 1; "Methods in Protein Chemistry, part D", written by Haruaki Yajima, Shumpei Sakakibara, edited by Society of Biochemistry of Japan, published by Tokyo Kagaku Dojin (1977); and Nobuo Izumiya et al., "Basis and Experiment of Peptide Synthesis", published by Maruzen K.K. (1985). As the synthetic method of the calcitonin derivative of the present invention, the solid phase method is preferred.

In the following, the case of synthesizing the calcitonin derivative of the present invention according to the solid phase method is to be described.

(1) First, Pro, the C-terminal amino acid of the desired calcitonin derivative, is bound to an insoluble resin. Subsequently, protective amino acids are successively bound from the C-terminal side according to the amino acid sequence of said derivative to obtain a protected peptide resin. As the insoluble resin, any of those known in this field of art can be used. For example, chloromethyl resin, hydroxymethyl resin and benzhydrylamine resin (BHA resin) each of which eliminatable with HF, 4-(oxymethyl)-phenoxymethyl resin and 4-(aminomethyl)phenoxymethyl resin each of which eliminatable with TFA, etc. can be employed, and BHA resin or 4-(aminomethyl)phenoxymethyl resin is particularly preferred, since they can give directly amides through cleavage between said resin and the peptide chain.

The "protected amino acid" is an amino acid with the functional group protected with a protective group by the known method, and various protected amino acids are commercially available. In the case of synthesizing the calcitonin derivative of the present invention, it is preferred to select either one of the protective groups shown below. First, the protective group for α-amino group is Boc or Fmoc. The protective group for the hydroxyl group of Ser or Thr is Bu$^t$ or Bzl. The protective group for the hydroxyl group of Tyr is Cl$_2$.Bzl, Bu$^t$ or it may not be protected. The protective group for the ε-amino group of lysine is Z, Cl.Z, Boc or Npys. The protective group for the carboxyl group of Glu or Asp is OBzl, OBu$^t$ or OcHex. The protective group for the guanidino group of Arg is Tos, NO$^2$ or Mtr. The protective group for the imidazolyl group of His is Tos or Fmoc. The protective group for Met may be oxygen, but it is preferably not protected. The protective group for the indolyl group of Trp is For or it may not be protected. The protective group for the mercapto group of Cys is Bzl, M.Bzl, 4CH$_3$.Bzl, Acm, Trt, Npys, Bu$^t$ or SBu$^t$. Among the protective groups for mercapto group, there are protective groups such as CM, CA, AE, etc. which are introduced by the reaction between mercapto group and modifying agents as described below, but they are not preferably used in the solid phase method. Each protective group is required to be selected suitably depending on the synthetic conditions of the peptide.

Oct, Kpc, etc. which are cyclic amino acids corresponding to the cyclic amino acid residues represented by the above formula (I) can be synthesized according to the known method. The synthesis can be performed according to the methods as described in, for example, Japanese Patent Publication No. 20837/1966; J. Cromatogr., 294 (1984), p. 413; Bull. Chem. Soc. Japan, 36 (1963), p. 920; Japanese Provisional Patent Publication No. 116465/1977, etc. In the case of Oct, for example, it is synthesized according to the method shown below.

Cysteine or its salt is suspended in water, and a carboxymethylating agent such as monoiodoacetamide, monobromoacetamide, etc. is added. An appropriate base, for example, an inorganic base such as sodium hydroxide, sodium phosphate, sodium carbonate, ammonium hydroxide or an organic base such as TEA, dicyclohexylamine, etc. is added to adjust the mixed solution to a pH of 6 to 10, preferably 7 to 9. At a reaction temperature of 20° to 60° C., preferably room temperature to 50° C., the reaction is carried out for a reaction time of 0.1 to 10 hours, preferably 0.5 to 5 hours, to effect carbamoylmethylation of the mercapto group of cysteine. Subsequently, the reaction mixture is subjected to the reaction in a sealed tube at a reaction temperature of 60° to 150° C., preferably 80° to 120° C., for a reaction time of 0.5 to 50 hours, preferably 1 to 10 hours, to obtain Oct. The Oct obtained is purified by use of such method as recrystallization, various chromatographic methods, etc.

Bonding of the protected amino acid can be effected by conventional condensation methods such as the DCC method, the active ester method, the mixed or symmetric acid anhydride method, the carbonyldiimidazole method, the DCC-HOBt method, the diphenylphosphorylazide method, etc., but the DCC method, the DCC-HOBt method and the symmetric acid anhydride method are preferred. These condensation reactions are generally carried out in an organic solvent such as DCM, DMF, chloroform, DMSO, benzene, or a mixed solvent thereof. It is preferred to carry out such reaction in DCM, DMF or a solvent mixture thereof. As the eliminating reagent of the protective group of α-amino group, TFA/DCM, HCl/dioxane, piperidine/DMF, etc. may be employed, and may be selected depending on the kind of said protective group. The extent of the progress of the condensation reaction in the respective stages of synthesis may be examined according to the method of E. Kaiser et al. [Anal. Biochem., 34. p. 595 (1970)](the ninhydrin reaction method).

As described above, a protected peptide resin having a desired amino acid sequence is obtained, and specific examples thereof are shown below.

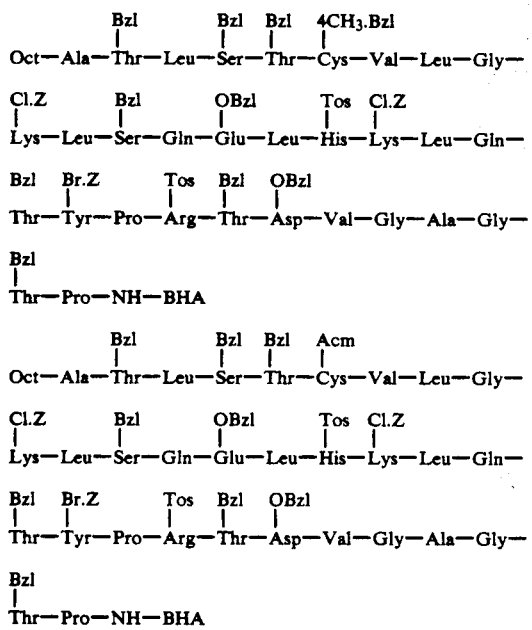

The desired calcitonin derivative is given by means of eliminating the peptide from the resin, and further treating the peptide with a reagent capable of eliminating protective groups other than mercapto group, for example, HF, TFA, etc. (the final deprotecting reaction).

(2) On the other hand, in the case of using a protective group eliminatable under the final deprotecting conditions described above as the protective group for the mercapto group of Cys at the 7-position, a peptide with free mercapto group of Cys is obtained by the final deprotecting reaction of the protective peptide resin. The peptide itself is also included within the calcitonin derivative of the present invention, and the peptide can be allowed to react with a modifying agent in a buffer to protect the mercapto group, whereby the calcitonin derivative of the present invention, protected Cys at the 7-position protected can be obtained. As the modifying agent, any compound capable of introducing a protective group through the reaction with mercapto group may be used. For example, there may be employed alkylating or arylating agents such as monoiodoacetic acid, monobromoacetic acid, monoiodoacetamide, ethyleneimine, acrylonitrile, vinyl pyridine, etc.; asymmetric disulfide forming agents such as 5,5'-dithiobis(2-nitro)benzoic acid or 2,2'-dipyridyldisulfide, etc.; N-ethylmaleimide, 2-nitro-5-thiocyanobenzoic acid, etc. The modification reaction may be carried out in a buffer generally of pH 2 to 11, preferably 6 to 9. The buffer to be used in such a reaction is known, including, for example, citric acid-sodium citrate, acetic acid-sodium acetate, phosphate, imidazole-hydrochloric acid, Tris-HCl, borate, diethanolamine-hydrochloric acid, glycine-sodium hydroxide, etc. The conditions for the modification reaction may vary depending on the kind of the modifying agent. For example, when monoiodoacetamide is used, various buffers generally of pH 6 to 10 may be employed. In this case, monoiodoacetamide is used generally at 0.1 to 10-fold equivalent of mercapto groups, preferably 1 to 2-fold equivalent, and the reaction temperature is generally 0° to 60° C., preferably 20° to 40° C., and the reaction time generally 0.1 to 10 hours, preferably 0.5 to 2 hours.

(3) Of the calcitonin derivatives of the present invention, the peptide in which the amino acid residue at the 1-position is Oct may be synthesized according to the method as shown below. That is, a protected peptide resin is synthesized by use of a eliminatable protective group under the final deprotecting conditions as mentioned above, for example, Cys protected with M.Bzl, 4CH3.Bzl in place of Oct. A specific example of the protected peptide resin is shown below.

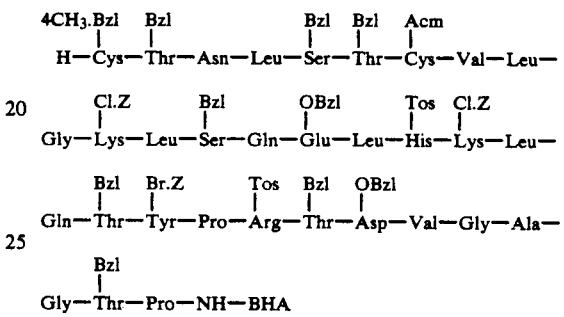

The protected peptide resin gives a peptide having free mercapto group by effecting the final deprotection according to the method as described above. The mercapto group of the peptide is protected by carbamoylmethyl(CA)ation by use of a modifying agent such as monoiodoacetamide, monobromoacetamide, etc. By heating the carbamoylmethylated peptide in a buffer, the desired peptide can be obtained. The buffer to be used in such reaction is known as mentioned above, and its pH may be generally 2 to 10, preferably 3 to 7. The peptide concentration may be generally 0.1 to 100 μM, preferably 0.5 to 10 μM, and the reaction temperature may be generally 30° to 150° C., preferably 60° to 100° C., and the reaction time generally 0.1 to 100 hours, preferably 0.5 to 50 hours.

(4) Further, of the calcitonin derivatives of the present invention, the peptide in which the amino acid residue at the 7-position is Cys protected with carbamoylmethyl may be synthesized according to the method a described below.

A natural type calcitonin is allowed to react with an appropriate reducing agent in a basic aqueous solution to reduce the intramolecular disulfide bonds to liberate mercapto groups. Subsequently, according to the same method as in the above (3), the desired peptide is obtained. For the basic aqueous solution to be used in such reduction reaction, various buffers of pH 7 to 13 may be employed. As such a buffer, the same ones as described above may be employed. As the reducing agent, any compound generally used on organic chemistry may be employed. For example, thiols such as DTT, thioglycolic acid, 2-mercaptoethanol, etc., sodium borohydride, aluminum hydride, zinc, etc. may be included. For example, when DTT is employed, its amount used may be generally 0.1 to 100-fold equivalent of the peptide, preferably 1 to 10-fold equivalent, the reaction temperature may be generally 1° to 60° C., preferably 20° to 40° C., and the reaction time may be generally 1 to 24 hours, preferably 3 to 5 hours. In the modification reaction, the modifying agent such as monoiodoacetamide or monobromoacetamide may be added in an amount generally of 0.1 to 100-fold equivalent, preferably 1 to 2-hold equivalent based on the reducing agent.

The peptide thus obtained can be isolated and purified according to the conventional methods such as extraction, recrystallization, various chromatography (gel filtration, ion-exchange, partition, adsorption, reverse phase), electrophoresis, counter-current partition, etc., but the method according to the reverse phase high performance liquid chromatography (reverse phase HPLC) is the most effective.

The present invention is described in more detail by referring to the following Examples, but these Examples are not limitative of the present invention at all.

EXAMPLE 1

Synthesis (1) of

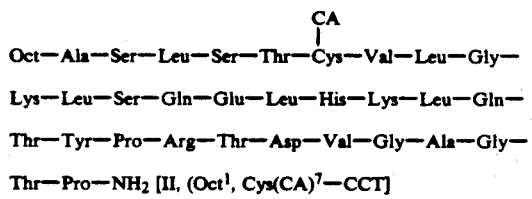

Oct—Ala—Ser—Leu—Ser—Thr—Cys—Val—Leu—Gly—

Lys—Leu—Ser—Gln—Glu—Leu—His—Lys—Leu—Gln—

Thr—Tyr—Pro—Arg—Thr—Asp—Val—Gly—Ala—Gly—

Thr—Pro—NH$_2$ [II, (Oct$^1$, Cys(CA)$^7$—CCT]

(1) Synthesis of 3-oxo-5-carboxyperhydro-1,4-thiazine

A solution of 1.75 g (10 mmole) of L-cysteine hydrochloride monohydrate dissolved in 50 ml of water was adjusted to pH 8.0 with 1M sodium carbonate. Under nitrogen gas stream, 1.85 g (10 mmole) of monoiodoacetamide and 1M sodium carbonate were added alternately while maintaining pH at 8.0. After the reaction was carried out at room temperature for 1 hour, further the reaction was carried out in a sealed tube at 100° C. for 2 hours. To the reaction mixture was added 4N HCl to adjust the pH to 3.25, followed by concentration to dryness. The residue was extracted with hot ethanol, and after cooling, the crystals were collected by filtration and recrystallized from hot ethanol. Yield: 560 mg (34.8%), melting point: 182° to 184° C., Fab mass analysis $[M+H]^+ =162$.

(2) Introduction of proline into BHA resin

An amount of 2 g of BHA resin (produced by Peptide Kenkyusho, divinylbenzene 2%, 100 to 200 mesh, amino group equivalent: 0.61 meq/g) was placed in a reaction vessel for peptide solid phase synthesis (produced by Bega Co.), successively treated with each 30 ml of the solvents shown below, and filtered after each treatment.

DCM (three times, each 2 min)
MeOH (three times, each 1 min)
DCM (three times, each 2 min)
10% TEA/DCM solution (5 min, 10 min, each once)

Subsequently, the BHA resin was stirred together with 0.32 g (1.5 mmole) of Boc-pro dissolved in 15 ml of DCM for 2 minutes. A solution of 0.31 g (1.5 mmole) of DCC in 15 ml DCM was added, and the mixture was stirred for 120 minutes. The reaction mixture was stirred, and the Boc-Pro-resin was washed with each 30 ml of the following solvents and filtered.

DCM (three times, each 2 min)
MeOH (three times, each 2 min)
DCM (three times, each 2 min)

Further, a solution of 1.34 g (12.2 mmole) of 1-acetylimidazole in 30 ml of DCM was added to the Boc-Pro-resin and acetylation was effected over 12 hours. By this reaction, the unreacted amino groups in the BHA resin were modified, to give subsequently the N-terminal end of proline which becomes the reaction initiation point for addition extension of protective amino acids.

(3) Introduction of the 31-position threonine

The total amount of the Boc-Pro-resin obtained in (2) was washed with DCM (three times), MeOH (three times) and DCM (three times) each for 2 minutes and filtered. To the resin was added 30 ml of a 50% TFA solution (solvent: DCM) and the mixture was stirred for 5 minutes, followed by filtration. Further, the resin was stirred under a similar TFA solution for 30 minutes to eliminate Boc groups. The resin obtained was successively treated with each 30 ml of the solvents shown below similarly as in (2), and filtered after each treatment.

DCM (three times, each 2 min)
MeOH (three times, each 2 min)
DCM (three times, each 2 min)
10% TEA/DCM solution (5 min, 10 min, each once)
DCM (three times, each 2 min)

Subsequently, to the Pro-resin was added a solution of 0.46 g (1.5 mmole) of Boc-Thr(Bzl) in 15 ml DCM, and the mixture was stirred for 2 minutes. Next, a solution of 0.31 g of DCC in 15 ml DCM was added, and the mixture was stirred for 240 minutes. After the reaction, the mixture was washed with DCM (three times), MeOH (three times) and DCM (three times), each for 2 minutes, followed by filtration. A very minute amount of this resin was sampled and confirmed that the ninhydrin test was negative. Next, a part of the resin was sampled, and its C-terminal amino acid bound content was measured to be 0.15 mmole/g.

(4) Introduction of respective amino acids at the 30 to 1 positions

Similarly as described in (3), the Boc-Thr(Bzl)-Pro-resin was coupled successively with the protective amino acids corresponding to the respective constituent amino acids from the 30-position to the 1-position of CT repesented by the above formula (II). Table 1 shows the protective amino acids and their amounts used in the respective reaction steps.

The coupling reaction was conducted twice with the same amounts of the protective amino group, and the coupling reaction time was made 120 minutes for the first time and 300 minutes for the second time. Here, Lys was used as Boc-Lys(Cl.Z) by eliminating TBA of Boc-Lys(Cl.Z)TBA (produced by Peptide Kenkyusho). Since Boc-Leu.H$_2$O and Oct were difficultly soluble in DCM single solvent, Boc- Leu.H$_2$O was used by dissolving in a solvent mixture of DMF and DCM (1:4), and Oct in DMF. Further, DMF was used in place of DCM for the washing solvent during coupling of Oct. In introduction of Gln at the 14- and 20-positions, 0.23 g of HOBt and 0.37 g of Boc-Gln were added into the reaction vessel at the same time.

After introduction of the amino acid of the 1-position, the operation of eliminating Boc groups was conducted similarly as in (2). The resin peptide was dried under reduced pressure overnight to obtain a dry resin peptide.

TABLE 1

Protective amino acids used in Example 1 and amounts thereof

| Position of amino acid | Protective amino acid | Molecular weight | Amounts used per single coupling (g) | Remarks |
|---|---|---|---|---|
| 30 | Boc—Gly | 175.1 | 0.26 | |
| 29 | Boc—Ala | 189.2 | 0.28 | |
| 28 | Boc—Gly | 175.1 | 0.26 | |
| 27 | Boc—Val | 217.2 | 0.33 | |
| 26 | Boc—Asp(OBzl) | 323.3 | 0.48 | |
| 25 | Boc—Thr(Bzl) | 309.3 | 0.46 | |
| 24 | Boc—Arg(Tos) | 428.5 | 0.64 | |
| 23 | Boc—Pro | 215.0 | 0.32 | |
| 22 | Boc—Tyr(Br.Z) | 494.3 | 0.74 | |
| 21 | Boc—Thr(Bzl) | 309.3 | 0.46 | |
| 20 | Boc—Gln | 246.2 | 0.37 | 0.23 g of HOBT combinedly used |
| 19 | Boc—Leu.H$_2$O | 249.3 | 0.37 | |
| 18 | Boc—Lys(Cl.Z).TBA | 487.9 | 0.73 | |
| 17 | Boc—His(Tos) | 423.0 | 0.63 | |
| 16 | Boc—Leu.H$_2$O | 249.3 | 0.37 | |
| 15 | Boc—Glu(OBzl) | 337.3 | 0.51 | |
| 14 | Boc—Gln | 246.2 | 0.37 | 0.23 g of HOBT combinedly used |
| 13 | Boc—Ser(Bzl) | 295.3 | 0.44 | |
| 12 | Boc—Leu.H$_2$O | 249.3 | 0.37 | |
| 11 | Boc—Lys(Cl.Z).TBA | 487.9 | 0.73 | |
| 10 | Boc—Gly | 175.1 | 0.26 | |
| 9 | Boc—Leu.H$_2$O | 249.3 | 0.37 | |
| 8 | Boc—Val | 217.2 | 0.33 | |
| 7 | Boc—Cys(4CH$_3$.Bzl) | 325.4 | 0.49 | |
| 6 | Boc—Thr(Bzl) | 309.3 | 0.46 | |
| 5 | Boc—Ser(Bzl) | 295.3 | 0.44 | |
| 4 | Boc—Leu.H$_2$O | 249.3 | 0.37 | |
| 3 | Boc—Ser(Bzl) | 295.3 | 0.44 | |
| 2 | Boc—Ala | 189.2 | 0.28 | |
| 1 | Oct | 161.2 | 0.24 | |

(5) Decomposition with HF

A part (200 mg) of the dried resin peptide was weighed, placed in a reaction vessel for HF decomposition (made of Teflon, trade name) and, with addition of 1.0 ml of anisol, left to stand overnight to swell the resin. The above reaction vessel having a stirrer placed therein was mounted on a HF decomposition device (produced by Peptide Kenkyusho), placed in a dry ice-ethanol bath and 10 ml of HF was introduced into the reaction vessel. The mixture was stirred in an ice-bath at 0° C. for 1 hour. Under reduced pressure, HF was gradually evaporated. After 3 hours, the reaction vessel was dismantled, and the deprotected peptide was taken out from the reaction vessel by use of diethyl ether, and washed with diethyl ether. The deprotected peptide was added into 20 ml of 2 M acetic acid to dissolve the deprotected peptide.

(6) Carbamoylmethylation of mercapto groups

The solution was filtered and adjusted to pH 8.0 with aqueous ammonia (40 ml). With addition of 30.8 mg of DTT, the mixture was stirred at 37° C. for 4 hours. By this reduction operation, the dimers which can be possibly be formed by oxidation of mercapto groups are returned to monomers. Next, 37.0 mg of monoiodoacetic acid was added, and the reaction was carried out in a dark place at 37° C. for 30 minutes.

The reaction mixture was adsorbed on a column (ODS column, $\phi$: 2×30 cm) filled with octadecylsilica, washed with water and then the peptide was eluted with 60% acetonitrile solution. The eluate was lyophilized to obtain 26.8 mg of crude (Oct$^1$, Cys(CA)$^7$)-CCT.

(7) Purification of crude (Oct$^1$, Cys(CA)$^7$)-CCT

The crude (Oct$^1$, Cys(CA)$^7$)-CCT obtained was dissolved in a 1 M acetic acid (5 mg/ml) and purified by the reverse phase high performance liquid chromatography. Chemcopack ODS-H (trade name, $\phi$: 10 mm×250 mm) column produced by Chemco Co. was used, with the eluents employed being water (100) - 10% TFA (1) for the eluent A and water (40)-acetonitrile (60) - 10% TFA (1) for the eluent B, and the elution was effected under the linear concentration gradient from the eluent A to the eluent B. Here, the numerals within bracckets represent volume ratios. The fraction corresponding to (Oct$^1$, Cys(CA)$^7$)-CCT was collected and lyophilized to obtain 2.8 mg of white powder. The biological activity of the white powder obtained was assayed according to the method as described in Japanese Provisional Patent Publication No. 123500/1985. As the result, it was found to be 5400 MRC U/mg, as contrasted to the biological activity of the natural type CCT which was 4500 MRC U/mg. Its amino acid analytical values are shown in Table 2.

TABLE 2

Amino acid composition of (Oct$^1$, Cys(CA)$^7$)—CCT

| Amino acid | Molar ratio | Amino acid number |
|---|---|---|
| Asx** | 0.95 | 1 |
| Thr | 3.55 | 4 |
| Ser | 2.84 | 3 |
| Glx*** | 2.88 | 3 |
| Pro | 1.86 | 2 |
| Gly | 3.06 | 3 |
| Ala | 2.00 | 2 |
| Val | 1.96 | 2 |
| Leu | 5.00 | 5 |
| Tyr | 1.07 | 1 |
| Lys | 1.99 | 2 |
| His | 1.20 | 1 |
| Arg | 0.97 | 1 |
| Cys(CM)**** | 1.47 | 2 |

*calculated by converting Leu to 5.00.
**Asn and Asp
***Gln and Glu
****Oct and Cys(CA) are hydrolyzed and detected as Cys(CM).

The white powder obtained was assayed by high performance liquid chromatography.

Measurement conditions (1)

| Column: | Chemcopack ODS-H (trade name, $\phi$: 4.6 mm × 150 mm), produced by Chemco Co.; |
|---|---|
| Flow rate: | 1.0 ml/min; |
| Eluent: | eluent A (water:acetonitrile:10% TFA = 100:0:1) |
| | eluent B (water:acetonitrile:10% TFA = 40:60:1) | were used, and eluted by the linear gradient from the eluent A to the eluent B (30 min);
Measurement wavelength: 210 nm.

As the result, a single strong absorption based on a peptide was recognized at a retention time of 24.7 min, which was (Oct$^1$, Cys(CA)$^7$)-CCT of the present invention.

Next, 15 μg of this product was dissolved in 50 μl of an aqueous 1% ammonium hydrogen carbonate solution containing 5 μg of trypsin, and tripsin digestion was effected at 37° C. for 2 hours. The digested product was analyzed under the same conditions (1) as described above. As the result, peaks based on peptides at retention times 11.2 min, 11.9 min, 13.0 min and 18.9 min were detected. The results of Fab mass analysis of these peptides are shown in Table 3. As the result, (Oct[1], Cys(CA)[7])-CCT was found to be cleaved at the C-terminal sides of Lys and Arg as expectedly to give 4 peptide fragments, each of which exhibited the mass number ([M+H]+) coincident with the theoretical value.

TABLE 3

| Fab mass analysis of trypsin digested product of (Oct[1], Cys(CA)[7])—CCT | | |
|---|---|---|
| | Measured value | Theoretical value |
| $T_1$ | 716 | 716 |
| $T_2$ | 854 | 854 |
| $T_3$ | 777 | 777 |
| $T_4$ | 1178 | 1178 |

(in the Table, each of $T_1$, $T_2$, $T_3$ and $T_4$ represents the peptide showing the peak at the retention time of 11.2 min, 12.9 min, 13.0 min and 18.9 min, when the trypsin digested product of (Oct[1], Cys(CA)[7])—CCT was subjected to the reverse phase HPLC under the conditions of (1).)

The stability test of the present product was performed as described below.

The (Oct[1], Cys(CA)[7])-CCT was dissolved in 0.1 M sodium citrate buffer (pH 6.0) to a concentration of 10 μg/ml. One ml of this solution was left to stand in a sealed tube at 80° C. for 24 hours. By analysis according to the reverse phase HPLC by use of the measurement conditions (1), the eluted peak area A of the remaining (Oct[1], Cys(CA)[7])-CCT was determined. Similarly, the eluted peak area B of the (Oct[1], Cys(CA)[7])-CCT in the sample solution not subjected to the heat treatment was determined, and the ratio of A to B (%) was defined as the index. Similarly, the results of stability test of CCT and 1,7
Asu CCT are summarized in Table 4.

TABLE 4

| Stability test of (Oct[1], Cys(CA)[7])—CCT, Asu CCT and CCT | |
|---|---|
| | Stability (%) |
| (Oct[1], Cys(CA)[7])—CCT | 95 |
| 1,7 Asu CCT | 88 |
| CCT | 33 |

EXAMPLE 2

Snythesis (2) of

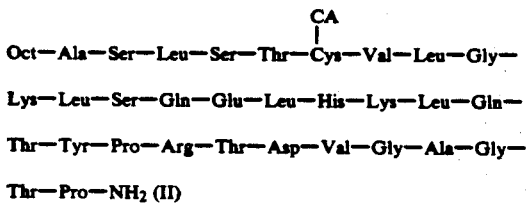

An amount of 200 μg of the natural type chicken CT represented by the formula:

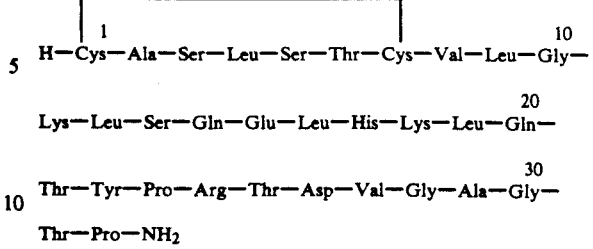

was weighed and dissolved in 150 μl of a 0.2 M Tris-HCl buffer (pH 8.2, containing 0.2% EDTA). Into this solution was added 100 μl of the same buffer containing 185 μg of DTT dissolved therein under nitrogen gas stream, and the reaction was carried out at 37° C. for 5 hours. Subsequently, 25 μl of 0.1 M NaOH containing 444 μg of monoiodoacetamide dissolved therein was added, and the reaction was carried out at 37° C. in a dark place for 30 minutes. The pH was adjusted to 2 to 3 by addition of 1 N AcOH. The mixture was purified by use of the reverse phase HPLC and the main peak was fractionated and lyophilized to obtain a peptide having the following structure:

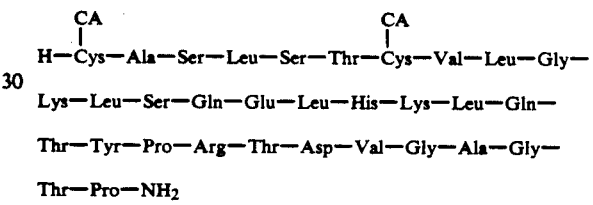

The conditions for the reverse phase HPLC are as follows:

| Column: | Chemcopack ODS-H (trade name, φ: 4.6 mm × 150 mm), produced by Chemco Co.; |
|---|---|
| Flow rate: | 1.0 ml/min; |
| Eluent: | eluent A (water:acetonitrile = 100:0) eluent B (water:acetonitrile = 60:40) were used, and eluted by the linear concentration gradient from the eluent A to the eluent B (30 min); |
| Measurement wavelength: 210 nm. | |

The peptide was dissolved (10 μg/ml concentration) in 0.2 M sodium citrate buffer (pH 6.0) and left to stand in a sealed tube at 80° C. for 24 hours. The reaction mixture was purified by use of the reverse phase HPLC (the conditions were the same as the measurement conditions (1)), and the main peak was fractionated and lyophilized to obtain 78.8 μg of white powder. The results of assay of the white powder according to the reverse phase HPLC, amino acid analysis and Fab mass analysis of trypsin digested product were identical with the (Oct[1], Cys(CA)[7])-CCT shown in Example 1. Also, the results of amino acid analysis and Fab mas analysis of the carboxypeptidase Y digested product of the N-terminal side fragment peptide obtained by trypsin digestion of the present peptide were identical with the (Oct[1], Cys(CA)[7])-CCT shown in Example 1. Thus, the present peptide was found to be (Oct[1], Cys(CA)[7])-CCT. When the biological activity of this peptide was mesured according to the method shown in Example 1, it was found to be equal to that obtained in Example 1.

EXAMPLE 3

Synthesis of

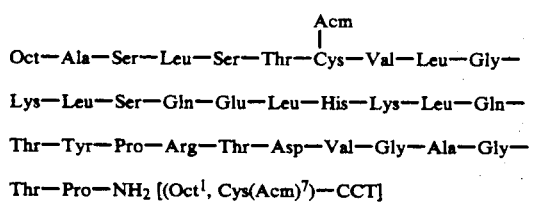

In introduction of the amino acid at the 7-position, 0.44 g (1.5 mmole) of Boc-Cys(Acm) was used in place of Boc-Cys (4CH$_3$.Bzl), and the solid phase synthesis was conducted under otherwise the same conditions as in Example 1 to obtain a protected peptide resin. A part (200 mg) of the protected peptide resin was subjected to HF decomposition in the same manner as in Example 1. The acetic acid solution of the peptide obtained was lyophilized as such to obtain 31.0 mg of crude (Oct$^1$, Cys(Acm)$^7$)-CCT. The peptide was purified according to the same method as in Example 1 - (7) to obtain 3.7 mg of (Oct$^1$, Cys(Acm)$^7$)-CCT. When the biological activity of this peptide was measured in the same manner as in Example 1, it was found to be 5500 MRC U/mg, as contrasted to the biological activity of the natural type CTT which was 4500 MRC U/mg.

EXAMPLE 4

Synthesis of

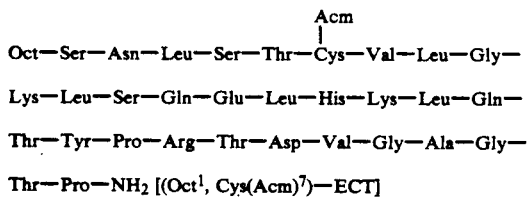

In introduction of the amino acids at the 2-position, 3-position and 7-position, 0.44 g (1.5 mmole) of Boc-Ser(Bzl) was used in place of Boc-Ala, 0.35 g of Boc-Asn and 0.23 g of HOBt in place of Boc-Ser(Bzl) and 0.44 g of Box-Cys(Acm) in place of Boc-Cys(4CH$_3$.Bzl), respectively, and the solid phase synthesis was conducted under otherwise the same conditions as in Example 1 to obtain a protected peptide resin. A part of the protected peptide resin was subjected to HF decomposition in the same manner as in Example 1 and the crude peptide obtained was purified according to the same manner as in Example 1 - (7) to obtain (Oct$^1$, Cys(Acm)$^7$)-ECT. When the biological activity of this peptide was measured in the same manner as in Example 1, it was found to be 5400 MRC U/mg, as contrasted to the biological activity of the natural type ECT which was 4500 MRC U/mg.

EXAMPLE 5

Synthesis was performed according to the same method as in Example 1 except for practicing no operation of protecting the mercapto groups, namely the monoiodoacetamide treatment after the HF decomposition treatment to obtain (Oct$^1$, Cys$^7$)-CCT of Example 1. When the stability and the biological activity of this peptide were measured similarly as in Example 1, they were found to be substantially equal to those of (Oct$^1$, Cys(CA)$^7$)-CCT of Example 1.

EXAMPLE 6

Synthesis was performed according to the same method as in Example 1 except for using 0.21 g (1.5 mmole) of Kpc in place of Oct in introduction of the amino acid at the 1-position to obtain (Kpc$^1$, Cys(CA)$^7$)-CCT. When the stability and the biological activity of this peptide were measured similarly as in Example 1, they were found to be substantially equal to those of (Oct$^1$, Cys(CA)$^7$)-CCT of Example 1.

EXAMPLE 7

Synthesis was performed according to the same method as in Example 1 except for using 0.19 g (1.5 mmole) of pGlu in place of Oct in introduction of the amino acid at the 1-position to obtain (pGlu$^1$, Cys(CA)$^7$)-CCT. When the stability and the biological activity of this peptide were measured similarly as in Example 1, they were found to be substantially equal to those of (Oct$^1$, Cys(CA)$^7$)-CCT of Example 1.

EXAMPLE 8

Snythesis of

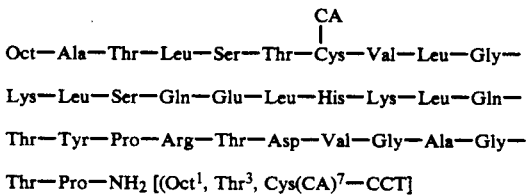

In the same manner as (1) to (5) in Example 1 except that in introduction of amino acid at the 3-position of (4) in Example 1 was replaced with that shown in the following Table 5, deprotected peptide dissolved in 2 M acetic acid was obtained.

TABLE 5

| Position of amino acid | Protective amino acid | Molecular weight | Amounts used per single coupling (g) |
|---|---|---|---|
| 3 | Boc—Thr(Bzl) | 309.3 | 0.46 |

(6) Carbamoylmethylation of mercapto groups

The solution was filtered and adjusted to pH 8.0 with aqueous ammonia (40 ml). With addition of 30.8 mg of DTT, the mixture was stirred at 37° C. for 4 hours. By this reduction operation, the dimers which can be possibly be formed by oxidation of mercapto groups are returned to monomers. Next, 37.0 mg of monoiodoacetic acid was added, and the reaction was carried out in a dark place at 37° C. for 30 minutes.

The reaction mixture was adsorbed on a column (ODS column, $\phi$: 2×30 cm) filled with octadecylsilica, washed with water and then the peptide was eluted with 60% acetonitrile solution. The eluate was lyophilized to obtain 26.8 mg of crude (Oct$^1$, Thr$^3$, Cys(CA)$^7$)-CCT.

(7) Purification of crude (Oct$^1$, Thr$^3$, Cys(CA)$^7$)-CCT

The crude (Oct$^1$, Thr$^3$, Cys(CA)$^7$)-CCT obtained was dissolved in a 1 M acetic acid (5 mg/ml) and purified by the reverse phase high performance liquid chromatography. Chemcopack ODS-H (trade name, φ: 10 mm×250 mm) column produced by Chemco Co. was used, with the eluents employed being water (100) - 10% TFA (1) for the eluent A and water (40) - acetonitrile (60) - 10% TFA (1) for the eluent B, and the elution was effected under the linear concentration gradient from the eluent A to the eluent B. Here, the numerals within bracckets represent volume ratios. The fraction corresponding to (Oct$^1$, Thr$^3$, Cys(CA)$^7$)-CCT was collected and lyophilized to obtain 3.3 mg of white powder. The biological activity of the white powder obtained was assayed according to the method as described in Japanese Provisional Patent Publication No. 123500/1985. As the result, it was found to be 7800 MRC U/mg, as contracted to the biological activity of the natural type CCT which was 4500 MRC U/mg. Further, its amino acid analytical values are shown in Table 6.

TABLE 6

Amino acid composition of (Oct$^1$, Thr$^3$, Cys(CA)$^7$)—CCT

| Amino acid | Molar ratio | Amino acid number |
|---|---|---|
| Asx** | 0.97 | 1 |
| Thr | 4.36 | 5 |
| Ser | 1.80 | 2 |
| Glx*** | 3.00 | 3 |
| Pro | 1.58 | 2 |
| Gly | 3.05 | 3 |
| Ala | 2.02 | 2 |
| Val | 1.88 | 2 |
| Leu | 5.00 | 5 |
| Tyr | 0.99 | 1 |
| Lys | 1.92 | 2 |
| His | 1.01 | 1 |
| Arg | 0.90 | 1 |
| Cys(CM)**** | 1.48 | 2 |

*calculated by converting Leu to 5.00.
**Asn and Asp
***Gln and Glu
****Oct and Cys(CA) are hydrolyzed and detected as Cys(CM).

The white powder obtained was assayed by high performance liquid chromatography in the same manner as in Example 1.

As the result, a single strong absorption based on a peptide was recognized at a retention time of 23.6 min, which was (Oct$^1$, Thr$^3$, Cys(CA)$^7$)-CCT of the present invention.

The result of Fab Mass analysis of the present peptide is shown below:
Observed value ([M+H]+) 3484.4
Theoretical value ([M+H]+) 3483.8

EXAMPLE 9

Synthesis of

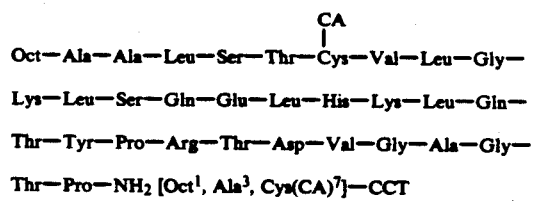

Oct—Ala—Ala—Leu—Ser—Thr—Cys—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH$_2$ [(Oct$^1$, Ala$^3$, Cys(CA)$^7$]—CCT

In introduction of the amino acid at the 3-position, solid phase synthesis was carried out in the same conditions as in Example 8 except for using 0.28 g of Boc-Ala in place of Boc-Thr(Bzl), a protected peptide resin was obtained. A part (50 mg) of the protected peptide resin was subjected to HF decomposition in the same manner as in Example 1. The crude peptide obtained was purified in the same manner as in Example 8 - (7), 0.9 mg of (Oct$^1$, Ala$^3$, Cys(CA)$^7$)-CCT was obtained.

EXAMPLE 10

Synthesis of

Oct—Ala—Thr—Leu—Ser—Thr—Cys(Acm)—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH$_2$ [(Oct$^1$, Thr$^3$, Cys(Acm)$^7$—CCT]

In the same manner as (1) to (4) in Example 1 except that in introduction of amino acid at the 3- and 7-positions of (4) in Example 1 were replaced with those shown in the following Table 7, deprotected peptide dissolved in 2 M acetic acid was obtained.

TABLE 7

| Position of amino acid | Protective amino acid | Molecular weight | Amounts used per single coupling (g) |
|---|---|---|---|
| 7 | Boc—Cys(Acm) | 292.3 | 0.44 |
| 3 | Boc—Thr(Bzl) | 309.3 | 0.46 |

(5) Decomposition with HF

A part (50.7 mg) of the dried resin peptide was weighed, placed in a reaction vessel for HF decomposition (made of Teflon, trade name) and, with addition of 0.5 ml of anisol, left to stand overnight to swell the resin. The above reaction vessel having a stirrer placed therein was mounted on a HF decomposition device (produced by Peptide Kenkyusho), placed in a dry ice-ethanol bath and 5 ml of HF was introduced into the reaction vessel. The mixture was stirred in an ice-bath at 0° C. for 1 hour. Under reduced pressure, HF was gradually evaporated. After 3 hours, the reaction vessel was dismantled, and the deprotected peptide was taken out from the reaction vessel by use of diethyl ether, and washed with diethyl ether. The deprotected peptide was added into 20 ml of 2 M acetic acid to dissolve the deprotected peptide.

The solution was passed through a Dowex (trade name) column of 1×2 cm (AcO-) and the eluate was lyophilized to obtain 19.2 mg of crude (Oct$^1$, Thr$^3$, Cys(Acm)$^7$)-CCT.

(6) Purification of crude (Oct$^1$, Thr$^3$, Cys(Acm)$^7$)-CCT

The crude (Oct$^1$, Thr$^3$, Cys(Acm)$^7$)-CCT obtained was dissolved in a 1 M acetic acid and purified by the reverse phase high performance liquid chromatography. Chemcopack ODS-H (trade name, φ: 10 mm×250 mm) column produced by Chemco Co. was used, with the eluents employed being water (100) - 10% TFA (1) for the eluent A and water (40) -acetonitrile (60) - 10 % TFA (1) for the eluent B, and the elution was effected under the linear concentration gradient from the eluent A to the eluent B. Here, the numerals within braccketts represent volume ratios. The fraction corresponding to (Oct$^1$, Thr$^3$, Cys(Acm)$^7$)-CCT was collected and lyophilized to obtain 1.75 mg of white powder.

Its amino acid analytical values are shown in Table 8.

TABLE 8

Amino acid composition of (Oct$^1$, Thr$^3$, Cys(Acm)$^7$)—CCT

| Amino acid | Molar ratio | Amino acid number |
|---|---|---|
| Asx** | 1.02 | 1 |
| Thr | 4.21 | 5 |
| Ser | 1.76 | 2 |
| Glx*** | 2.92 | 3 |
| Pro | 1.96 | 2 |
| Gly | 3.02 | 3 |
| Ala | 1.99 | 2 |
| Val | 1.94 | 2 |
| Leu | 5.00 | 5 |
| Tyr | 0.98 | 1 |
| Lys | 1.96 | 2 |
| His | 1.04 | 1 |
| Arg | 0.97 | 1 |
| Cys(CM)**** | 0.38 | 1 |

*calculated by converting Leu to 5.00.
**Asn and Asp
***Gln and Glu
****Oct is hydrolyzed and detected as Cys(CM).

The white powder obtained was assayed in the same manner as in Example 1.

As the result, a single strong absorption based on a peptide was recognized at a retention time of 30.0 min, which was (Oct$^1$, Thr$^3$, Cys(Acm)$^7$)-CCT of the present invention.

The result of Fab Mass analysis of the present peptide is shown below:
Observed value ([M+H]+) 3497.2
Theoretical value ([M+H]+) 3497.8

EXAMPLE 11

Synthesis of pGlu—Ala—Thr—Leu—Ser—Thr—Cys(Acm)—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH$_2$ [pGlu$^1$, Thr$^3$, Cys(Acm)$^7$]—CCT In introduction of the amino acid at the 1-position, solid phase synthesis was carried out in the same conditions as in Example 10 except for using 0.19 g of pGlu in place of Oct, a protected peptide resin was obtained. A part of the protected peptide resin was subjected to HF decomposition in the same manner as in Example 10. The crude peptide obtained was purified in the same manner as in Example 10 - (6), 1.79 mg of (pGlu$^1$, Thr$^3$, Cys(Acm)$^7$)-CCT was obtained.

The biological activity of the present peptides obtained in Examples 8 to 11 was assayed according to the method in the same manner as in Example 1, and compared it with those of 1,7
Asu CCT and CCT. The results are shown in Table

TABLE 9

| Name of peptide | Activity (MRC U/mg) |
|---|---|
| (Oct$^1$, Thr$^3$, Cys(CA)$^7$)—CCT | 7800 |
| (Oct$^1$, Ala$^3$, Cys(CA)$^7$)—CCT | 6100 |
| (Oct$^1$, Thr$^3$, Cys(Acm)$^7$)—CCT | 7800 |
| (pGlu$^1$, Thr$^3$, Cys(Acm)$^7$)—CCT | 7500 |
| (Oct$^1$, Cys(CA)$^7$)—CCT | 5400 |
| Asu CCT | 4700[1] |
| CCT | 4500[2] |

[1] Y. Sako, M. Shibara, et al., Peptide Chemistry 1986, 169 (1985)
[2] M. Homma, M. Watanabe, et al., J. Biochem., 100, 459 (1986)

Also, the stability test of the present product was performed in the same manner as in Example 1. Similarly, the results of stability test of CCT and 1,7
Asu CCT are summarized in Table 10.

TABLE 10

Stability test

| Name of peptide | Stability (%) |
|---|---|
| (Oct$^1$, Thr$^3$, Cys(CA)$^7$)—CCT | 95 |
| (Oct$^1$, Ala$^3$, Cys(CA)$^7$)—CCT | 90 |
| (Oct$^1$, Thr$^3$, Cys(Acm)$^7$)—CCT | 82 |
| (pGlu$^1$, Thr$^3$, Cys(Acm)$^7$)—CCT | 90 |
| Asu CCT | 88 |
| CCT | 33 |

The method for preparation of the compounds as described in the foregoing description or in the respective Examples can be altered. For example, as the protected amino acids to be used, a large number of amino acids with different protective groups are commercially available. These commercially available protected amino acids can be used suitably changed, and all of the peptides obtained are equal to the calcitonin derivative of the present invention.

According to the present invention, a calcitonin derivative having a high activity and a high stability can be supplied stably and at low cost. Also, the calcitonin derivative of the present invention can be used as the reagent for experiments, further as the diagnostic agents by establishing an assay system by use thereof, and it can be also utilized as the pharmaceutical or animal medicine on the bases of the biological activity.

We claim:

1. A calcitonin derivative or a pharmaceutically acceptable salt thereof selected from the group consisting:

Oct—Ala—Ser—Leu—Ser—Thr—Cys(CA)—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH$_2$,

Oct—Ala—Ser—Leu—Ser—Thr—Cys(Acm)—Val—Leu—Gly—
Lys—Leu—Ser—Gln—Glu—Leu—His—Lys—Leu—Gln—
Thr—Tyr—Pro—Arg—Thr—Asp—Val—Gly—Ala—Gly—
Thr—Pro—NH$_2$,

Oct—Ser—Asn—Leu—Ser—Thr—Cys(Acm)—Val—Leu—Gly—
Lys—Leu—Ser—Gln—Glu—Leu—His—Lys—Leu—Gln—

-continued

Thr—Tyr—Pro—Arg—Thr—Asp—Val—Gly—Ala—Gly—Thr—Pro—NH₂,

Oct—Ala—Thr—Leu—Ser—Thr—Cys(CA)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂,

Oct—Ala—Ala—Leu—Ser—Thr—Cys(CA)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂, pGlu—Ala—Ser—Leu—Ser—Thr—Cys(CA)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂,

Oct—Ala—Thr—Leu—Ser—Thr—Cys(Acm)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂, pGlu—Ala—Thr—Leu—Ser—Thr—Cys(Acm)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂,

Kcp—Ala—Ser—Leu—Ser—Thr—Cys(CA)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂, and Oct—Ala—Ser—Leu—Ser—Thr—Cys—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂, Kcp-Ala-Ser-Leu-Ser-Thr wherein Ala represents alanine, Arg: arginine, Asn: asparagine, Asp: aspartic acid, Cys: cysteine, Gln: glutamine, Glu: glutamic acid, Gly: glycine, His: histidine, Ile: isoleucine, Leu: leucine, Lys: lysine, Met: methionine, Phe: phenylalanine, Pro: proline, Ser: serine, Thr: threonine, Trp: tryptophan, Try: tyrosine, Val: valine, Cys: cystine, Oct: 3-oxo-5-carboxyperhydro-1,4-thiazine, CA: carbamoylmethyl, Acm: acetamidomethyl, pGlu: pyroglutamic acid and Kpc: 2-keto-piperidine-6-carboxylic acid.

2. A calcitonin derivative or a pharmaceutically acceptable salt thereof according to claim 1, which is
Oct-Ala-Thr-Leu-Ser-Thr Oct—Ala—Thr—Leu—Ser—Thr—Cys(CA)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂, Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH₂, wherein Ala represents alanine, Arg: arginine, Asn: asparagine, Asp: aspartic acid, Cys: cysteine, Gln: glutamine, Glu: glutamic acid, Gly: glycine, His: histidine, Ile: isoleucine, Leu: leucine, Lys: lysine, Met: methionine, Phe: phenylalanine, Pro: proline, Ser: serine, Thr: threonine, Trp: tryptophan, Tyr: tyrosine, Val: valine, Cys: cystine, Oct: 3-oxo-5-carboxyperhydro-1,4-thiazine and CA: carbamoylmethyl.

3. A calcitonin derivative or a pharmaceutically acceptable salt thereof according to claim 1, which is
Oct-Ala-Ala-Leu-Ser-Thr Oct—Ala—Ala—Leu—Ser—Thr—Cys(CA)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂, Val-Leu-Gly-Lys-Leu-Ser-Gln-Glu-Leu-His-Lys-Leu-Gln-Thr-Pro-Arg-Thr-Asp-Val-Gly-Ala-Gly-Thr-Pr-NH₂, wherein Ala represents alanine, Arg: arginine, Asn: asparagine, Asp: aspartic acid, Cys: cysteine, Gln: glutamine, Glu: glutamic acid, Gly: glycine, His: histidine, Ile: isoleucine, Leu: leucine, Lys: lysine, Met: methionine, Phe: phenylalanine, Pro: proline, Ser: serine, Thr: threonine, Trp: tryptophan, Tyr: tyrosine, Val: valine, Cys: cystine, Oct: 30-oxo-5-carboxyperhydro-1,4-thiazine and CA: carbamoylmethyl.

4. A calcitonin derivative or a pharmaceutically acceptable salt thereof according to claim 1, wherein the calcitonin derivative is
Oct-Ala-Thr-Leu-Ser-Thr Oct—Ala—Thr—Leu—Ser—Thr—Cys(Acm)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂.

Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH₂.

5. A calcitonin derivative or a pharmaceutically acceptable salt thereof according to claim 1, wherein the calcitonin derivative is
pGlu-Ala-Thr-Leu-Ser-Thr pGlu—Ala—Thr—Leu—Ser—Thr—Cys(Acm)—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH₂.

Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH₂.

* * * * *